United States Patent [19]

Shah et al.

[11] Patent Number: 5,849,504
[45] Date of Patent: Dec. 15, 1998

[54] NUCLEIC ACID PROBES AND METHODS FOR DETECTING *PNEUMOCYSTIS CARINII*

[75] Inventors: Jyotsna Shah, Nashua, N.H.; Amelia Buharin, St. Paul, Minn.; David J. Lane, Milford; Jing Liu, Waltham, both of Mass.

[73] Assignee: Amoco Corporation, Chicago, Ill.

[21] Appl. No.: 452,145

[22] Filed: May 26, 1995

Related U.S. Application Data

[63] Continuation-in-part of Ser. No. 826,657, Jan. 21, 1992, Pat. No. 5,519,127, which is a continuation-in-part of Ser. No. 392,679, Aug. 11, 1989, abandoned.

[51] Int. Cl.$^6$ .......................... G01N 33/53; C07H 21/04; A61K 51/00
[52] U.S. Cl. .............................. 435/7.2; 435/6; 435/7.31; 435/7.92; 435/7.93; 435/7.94; 435/7.95; 536/24.32; 536/22.1; 536/23.1; 536/24.3; 424/1.11; 424/1.73
[58] Field of Search .................................. 536/22.1, 23.1, 536/24.32, 24.3; 424/1.1, 1.73, 1.11; 435/6, 7.2, 7.31, 7.92, 7.93, 7.94, 7.95

[56] References Cited

U.S. PATENT DOCUMENTS

| 4,801,536 | 1/1989 | Stahl et al. ................................. 435/68 |
| 4,851,330 | 7/1989 | Kohne .......................................... 435/6 |
| 4,857,637 | 8/1989 | Hammonds et al. ..................... 530/403 |
| 4,925,800 | 5/1990 | Kovacs et al. . |
| 5,198,421 | 3/1993 | Chen et al. . |
| 5,306,798 | 4/1994 | Schwartz et al. . |
| 5,519,127 | 5/1996 | Shah et al. ............................ 536/24.32 |

FOREIGN PATENT DOCUMENTS 9102092  12/1991  WIPO .

OTHER PUBLICATIONS

Edman et al., Nature, vol. 334, pp. 519–522, (1988).
Imajoh et al., Biochemistry, vol. 27, pp. 8122–8128, (1988).
Kirchgessner et al., J. of Biol. Chem., vol. 262, No. 18, pp. 8463–8469, (1987).
Michaels et al., Eur. J. of Biol., vol. 166, pp. 55–61 (1987).
Kunai et al., Eur. J. Biochem., V. 160, pp. 433–440 (1986).
L. Medlin et al., "The characterization of enzymatically amplified eukaryotic 16S–like rRNA–coding regions", Gene, vol. 71, 1988, pp. 491–499.
S. L. Stringer et al., "Pneumocystis carinii: Sequence from Ribosomal RNA Implies a Close Relationship with Fungi", Experimental Parasitology, vol. 68, 1989, pp. 45–461.
K. Tanabe et al., "Use of Pneumocystis carinii Genomic DNA Clones for DNA Hybridization Analysis of Infected Human Lungs", The Journal of Infectious Diseases, vol. 157, No. 3, 1988, pp. 593–596.

*Primary Examiner*—James O. Wilson
*Attorney, Agent, or Firm*—Norval B. Galloway

[57] ABSTRACT

The invention features nucleic acid probes and methods for detecting *Pneumocystis carinii* (e.g., human or ferret *P. carinii*) in hybridization assays.

16 Claims, No Drawings

NUCLEIC ACID PROBES AND METHODS FOR DETECTING *PNEUMOCYSTIS CARINII*

This application is a continuation-in-part of U.S. patent application Ser. No. 07/826,657, filed Jan. 21, 1992, which issued as U.S. Pat. No. 5,519,127 on May 21, 1996; which is a file wrapper continuation-in-part of U.S. patent application Ser. No. 07/392,679, filed Aug. 8, 1989, now abandoned. U.S. patent application Ser. No. 07/826,657 which issued as U.S. Pat. No. 5,519,127 on May 21, 1996, is herein incorporated by reference in its entirety.

BACKGROUND OF THE INVENTION

This invention relates to nucleic acid probes and methods for detecting *Pneumocystis carinii*.

*Pneumocystis carinii* is a small unicellular fungus that infects the lower respiratory tract of most mammals, including humans. Although it is rarely a cause of illness in normal individuals, *P. carinii* infection characteristically gives rise to life threatening interstitial pneumonia in certain conditions of immunodeficiency, and is one of the most common causes of morbidity and mortality in acquired immune deficiency syndrome.

SUMMARY OF THE INVENTION

We have generated nucleic acid probes which discriminate between different species of *P. carinii* in hybridization assays.

Accordingly, in a first aspect, the invention features a nucleic acid fragment to be used as a probe for detecting human or ferret *P. carinii* in a hybridization assay. A probe of the invention discriminates between human or ferret *P. carinii*, and rat *P. carinii*, which means that the probe binds to nucleic acid (e.g., rRNA or rDNA) from human or ferret *P. carinii* more favorably than to nucleic acid from rat *P. carinii*.

In a second aspect, the invention features a nucleic acid fragment containing a sequence selected from at least ten, thirteen, or fifteen consecutive nucleotides, or the entire sequence, of a probe selected from 3198, 3200, PC300, 1484, 1493, 1494, 1495, 1496, or 1497, or the full length complementary sequence thereof.

In a third aspect, the invention features a nucleic acid fragment containing a sequence selected from at least ten, thirteen, or fifteen consecutive nucleotides, or the entire sequence, of probe 3198, or the full length complementary sequence thereof.

In a fourth aspect, the invention features a nucleic acid fragment containing a sequence selected from at least ten, thirteen, or fifteen consecutive nucleotides, or the entire sequence, of probe 3200, or the full length complementary sequence thereof.

In fifth aspect, the invention features a method for detecting *P. carinii* in a sample. In this method, a sample is contacted with a probe that discriminates between human or ferret *P. carinii*, and rat *P. carinii*, under conditions that permit the probe to hybridize to human or ferret *P. carinii* nucleic acid (e.g., rRNA or rDNA). Detection of the probe bound to the *P. carinii* nucleic acid in the sample is used as an indication of the presence of human or ferret *P. carinii* in the sample.

In a final aspect, the invention features a method for detecting the presence of *P. carinii* in a sample. In this method, a sample is contacted with a nucleic acid fragment containing a sequence selected from at least ten, thirteen, or fifteen consecutive nucleotides, or the entire sequence, of a probe selected from 3198, 3200, PC300, 1484, 1493, 1494, 1495, 1496, or 1497, or the full length complementary sequence thereof; under conditions that permit the nucleic acid fragment to hybridize to *P. carinii* nucleic acid. Detection of the nucleic acid fragment bound to the *P. carinii* nucleic acid in the sample is used as an indication of the presence of *P. carinii* in the sample.

In one embodiment of this aspect of the invention, the nucleic acid fragment contains a sequence selected from at least ten, thirteen, or fifteen consecutive nucleotides, or the entire sequence, of probe 3198, or the full length complementary sequence thereof.

In a second embodiment of this aspect of the invention, the nucleic acid fragment contains a sequence selected from at least ten, thirteen, or fifteen consecutive nucleotides, or the entire sequence, of probe 3200, or the full length complementary sequence thereof.

An advantage of probes 3198 and 3200 is that while they detect all three species of human *P. carinii* tested, and thus are not limited to detecting a single human *P. carinii* strain, they do not detect rat or ferret *P. carinii*.

Other features and advantages of the present invention will be apparent from the following detailed description thereof, and also from the appended claims.

DETAILED DESCRIPTION OF THE INVENTION

The invention features nucleic acid probes for detecting *P. carinii* (e.g., human or ferret *P. carinii*) in hybridization assays. The probes of the invention may be used in methods for detecting the presence of *P. carinii* in a biological sample. In these methods, a probe of the invention is contacted with a biological sample (e.g., induced sputum, bronchial lavage, or a tissue sample) in a hybridization assay, and detection of the probe bound to the nucleic acid in the sample is used as an indication of the presence of *P. carinii* in the sample.

Probes included in the invention may be identified by (1) preparing a nucleic acid fragment (i.e., a probe) corresponding to, or complementary to, a sequence of at least ten nucleotides of nucleic acid from human or ferret *P. carinii*, and (2) comparing the ability of the probe to detect human or ferret *P. carinii*, to its ability to detect rat *P. carinii*, in a hybridization assay. Probes which hybridize to human or to ferret *P. carinii* more favorably than to rat *P. carinii* are included in the invention.

Human and ferret *P. carinii* nucleic acid may be obtained from, e.g., biological samples (such as induced sputum or bronchial lavage) from infected individuals, using standard methods in the art. For example, DNA encoding *P. carinii* ribosomal RNA may be obtained by PCR amplification of DNA prepared from a bronchial lavage sample of an infected patient using the methods and primers described in USSN 07/826,657.

Any human or ferret *P. carinii* sequence (e.g., a sequence encoding 5S, 5.8S, 18S, or 28S ribosomal RNA) may be selected as a candidate sequence for the identification of probes. Preferred sequences are those which diverge from analogous sequences in non-human and/or non-ferret *P. carinii*, or other fungi, as determined by phylogenetic comparison.

The nucleic acid probes of the invention are at least 10 nucleotides in length, and may contain deoxyribonucleotides (DNA probes), ribonucleotides (RNA probes), or combinations or modifications thereof. The probes may be single stranded or double stranded, and may be prepared by any of a number of standard methods in the art. For example, the probes may be made by chemical synthesis, restriction endonuclease digestion of a vector (e.g., a plasmid containing a sequence corresponding to the probe), polymerase chain reaction (PCR) amplification, or in vitro transcription of a vector containing a sequence corresponding to the probe (see, e.g., Ausubel et al., Current Protocols in Molecular Biology, Greene Publishing, New York, N.Y. (1994)).

The probes may be labeled during or after synthesis. For example, labeled nucleotides containing, e.g., radioisotopes (e.g., $P^{32}$, $S^{35}$, or $H^3$), biotin, or digoxigenin, may be incorporated into the probe during synthesis. Probes containing biotin are detected by the use of a secondary reagent, such as avidin or streptavidin, which contains a detectable label, such as a fluorochrome (e.g., fluorescein or rhodamine) or an enzyme (e.g., alkaline phosphatase or horseradish peroxidase). Similarly, probes containing digoxigenin may be detected by using a labeled antidigoxigenin antibody. Probes may also be labeled after synthesis by, e.g., nick translation or the use of T4 RNA ligase, poly(A) polymerase, terminal transferase, or T4 polynucleotide kinase, in standard methods (see, e.g., Ausubel et al., supra).

The probes may also contain modified nucleotides in order to increase the stability of the probe. For example, ribonucleotides containing 2'—O—alkyl groups on the ribose group may be used. The probes may also contain modifications which facilitate capture of the probe onto a solid support. For example, poly-dA or poly-deazaguanosine tails may be added to the 3' ends of the probes, using terminal transferase, in order to facilitate probe binding to a solid support, e.g., poly-dT or poly-dC labeled magnetic particles.

The probes may be purified prior to use, using standard methods, such as denaturing polyacrylamide gel electrophoresis, high performance liquid chromatography, or gel filtration chromatography (see, e.g., Ausubel et al., supra).

The probes of the invention may be used in any standard hybridization assay to detect the presence of P. carinii in a sample. For example, Southern blot, dot blot, in situ hybridization, or dual probe, sandwich-type hybridization assays may be used (see, e.g., USSN 07/826,657; PCT/US93/09703 (International Publication Number WO 94/10335)). Alternatively, the probes may be used as primers in a polymerase chain reaction assay (see, e.g., Ausubel et al., supra).

Biological samples that may be analyzed using the probes and methods of the invention include induced sputum, bronchial lavage, and tissue samples from, e.g., the lung or spleen. Nucleic acid is extracted from the sample by standard methods (except in the case of in situ hybridization, where the cells are kept intact), and is analyzed using the probes in the assays listed above. A single probe, or combinations of probes, may be used in the assay.

The hybridization conditions used with the probes, and in the methods, of the invention fall within the range of 0.5M–2M salt (e.g., NaCl) at 35° C.–65° C. As is known by one skilled in the art, selection of hybridization conditions depends on the length and nucleotide content (i.e., G/C compared to A/T) of the probe. Accordingly, hybridization conditions may be adjusted to accommodate these factors. In addition, the use of different salts (e.g., guanidine thiocyanate compared with NaCl), and denaturing agents (e.g., sodium dodecyl sulfate) may require adjustment of the salt concentration and the temperature, as can readily be determined by one skilled in the art.

Examples of hybridization conditions that may be used in the present invention are as follows. In dot blot and Southern analysis, the following hybridization conditions may be used: 60° C. for 14–16 hours in 0.9M NaCl, 0.12M Tris—HCl (pH 7.8), 6 mM EDTA, 0.1M $KPO_4$, 0.1% SDS, 0.1% pyrophosphate, 0.002% ficoll, 0.02% BSA, and 0.002% polyvinylpyrrolidine. After hybridization, the filters are washed using standard methods. For example, three 15 minute post-hybridization washes at 60° C. in 0.03M NaCl, 0.004M Tris, pH 7.8, 0.2 mM EDTA, and 0.1% SDS, may be carried out in order to remove unbound probes. For in situ hybridization, the following conditions may be used: 750 mM NaCl, 100 mM Tris—HCl (pH 7.8), 5 mM EDTA, 0.2% bovine serum albumin, 10% dextran sulfate, 1.7–2.0 ng/$\mu$l rhodamine-X labeled probe (see USSN 07/826,657).

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever.

P. carinii 18S rRNA-specific probes

Human P. carinii 18S rRNA-specific probes of the invention include probes 3198 and 3200, which have the sequences:

| | |
|---|---|
| 3198: 5'-CTTCGGAGGACCGGGCCGTCAA CCCCT-3' | (SEQ ID NO: 1) |
| 3200: 5'-CTTTCCAGCAATGGGTCATC-3' | (SEQ ID NO: 2) |

Hybridization of probes 3198 and 3200 to human, ferret, and rat P. carinii samples in Southern dot-blot analysis is shown in the Table below. In these experiments, equal molar amounts of nucleic acid from the indicated strains was spotted onto a nitrocellulose filter. In the case of human and ferret P. carinii samples, approximately 0.1 $\mu$g of a plasmid containing nucleotide sequences encoding the respective 18S rRNA subunits was used per spot (see USSN 07/826, 657). In the case of the rat P. carinii samples, approximately 0.1 $\mu$g total RNA was used per sample. The blots were hybridized with $P^{32}$ end-labeled probes under the hybridization conditions described above.

Washed hybridization filters were exposed to X-ray film, and the intensity of the hybridization signals was scored visually with respect to control samples containing equivalent molar amounts of P. carinii DNA. A scale of hybridization intensity ranging from "++++" (hybridization signal equivalent to that of control P. carinii sample for which a perfect match between the probe has been determined by sequence analysis) to "+" (barely detectable even after long (overnight to several days) exposure of X-ray film), or "−" (no hybridization) was used to compare hybridization signals between the different organisms and probes.

The invention also includes probe PC300, which is complementary to a portion of human 18S rRNA, and has the following sequence:

| | |
|---|---|
| PC300: 5'-ATGAATGACCAAAGTAAGCCCCG AA-3' | (SEQ ID NO: 3) |

Probes which hybridize to ferret P. carinii 18S rRNA (e.g., 1493, 1494, 1495, 1496, and 1497), as well as probe 1484 (see Table below), were described and characterized in USSN 07/826,657.

| Samples | 1484 | 3198 | 3200 | 1487 | 1488 |
|---|---|---|---|---|---|
| Human PC 1 | ++++ | ++++ | ++++ | ++++ | ++++ |
| Human PC 2 | ++++ | ++++ | ++++ | ++++ | ++++ |
| Rat PC RNA | ++ | − | − | + | ++++ |
| Ferret PC 71 | ++++ | − | − | + | ++++ |
| Ferret PC 101 | ++ | − | − | + | ++++ |
| Ferret PC 104 | + | − | − | + | + |

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for detecting the presence of *Pneumocystis carinii* in a sample, said method comprising the steps of:
   a) contacting said sample with a probe for detecting human or ferret *Pneumocystis carinii* in a hybridization assay, wherein said probe discriminates between human or ferret *Pneumocystis carinii* and rat *Pneumocystis carinii*, under conditions that permit said probe to hybridize to *Pneumocystis carinii* nucleic acid; and
   b) detecting said probe bound to said *Pneumocystis carinii* nucleic acid in said sample as an indication of the presence of *Pneumocystis carinii* in said sample.

2. A method for detecting the presence of *Pneumocystis carinii* in a sample, said method comprising the steps of:
   a) contacting said sample with a nucleic acid fragment comprising a sequence selected from at least ten consecutive nucleotides of a probe selected from 3198, 3200, PC300, 1484, 1493, 1494, 1495, 1496, or 1497, or the full length complementary sequence thereof,

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CTTCGGAGGA CCGGGCCGTC AACCCCT 27

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

CTTTCCAGCA ATGGGTCATC 20

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

ATGAATGACC AAAGTAAGCC CCGAA 25 under conditions that permit said nucleic acid fragment to hybridize to *Pneumocystis carinii* nucleic acid; and b) detecting said nucleic acid fragment bound to said *Pneumocystis carinii* nucleic acid in said sample as an indication of the presence of *Pneumocystis carinii* in said sample.

3. The method of claim 1, wherein said nucleic acid fragment comprises a sequence that is selected from at least ten consecutive nucleotides of probe 3198, or the full length complementary sequence thereof.

4. The method of claim 3, wherein said nucleic acid fragment comprises a sequence selected from at least thirteen consecutive nucleotides of probe 3198, or the full length complementary sequence thereof.

5. The method of claim 4, wherein said nucleic acid fragment comprises a sequence selected from at least fifteen consecutive nucleotides of probe 3198, or the full length complementary sequence thereof.

6. The method of claim 5, wherein said nucleic acid fragment comprises the entire sequence of probe 3198, or its full length complementary sequence.

7. The method of claim 1, wherein said nucleic acid fragment comprises a sequence selected from at least ten consecutive nucleotides of probe 3200, or the full length complementary sequence thereof.

8. The method of claim 7, wherein said nucleic acid fragment comprises a sequence selected from at least thirteen consecutive nucleotides of probe 3200, or the full length complementary sequence thereof.

9. The method of claim 8, wherein said nucleic acid fragment comprises a sequence selected from at least fifteen consecutive nucleotides of probe 3200, or the full length complementary sequence thereof.

10. The method of claim 9, wherein said nucleic acid fragment comprises the entire sequence of probe 3200, or its full length complementary sequence.

11. A nucleic acid fragment comprising a sequence selected from at least fifteen consecutive nucleotides of a probe selected from 3198, 3200, PC300, 1484, 1493, 1494, 1495, 1496, or 1497, or the full length complementary sequence thereof.

12. The nucleic acid fragment of claim 11, wherein said fragment comprises the entire sequence of said probe, or the full length complementary sequence thereof.

13. A nucleic acid fragment comprising a sequence selected from at least fifteen consecutive nucleotides of probe 3198, or the full length complementary sequence thereof.

14. The nucleic acid fragment of claim 13, wherein said fragment comprises the entire sequence of probe 3198, or the full length complementary sequence thereof.

15. A nucleic acid fragment comprising a sequence selected from at least fifteen consecutive nucleotides of probe 3200, or the full length complementary sequence thereof.

16. The nucleic acid fragment of claim 15, wherein said fragment comprises the entire sequence of probe 3200, or the full length complementary sequence thereof.

* * * * *